(12) United States Patent  (10) Patent No.: US 8,690,835 B1
Parris  (45) Date of Patent: Apr. 8, 2014

(54) GARMENT FOR ACCOMMODATING INTRAVENOUS CATHETERS AND GASTRONOMY TUBE

(76) Inventor: Nicole A. Parris, Chester, VA (US)

(*) Notice: Subject to any disclaimer, the term of this patent is extended or adjusted under 35 U.S.C. 154(b) by 0 days.

(21) Appl. No.: 13/364,094

(22) Filed: Feb. 1, 2012

(51) Int. Cl.
*A61M 25/02* (2006.01)

(52) U.S. Cl.
USPC .......... 604/174; 604/179; 2/111; 2/83; 2/114; 2/104; 2/300

(58) Field of Classification Search
USPC ......... 604/174, 179; 2/69.5, 914, 70, 75, 114, 2/83, 104, 11, 271
See application file for complete search history.

(56) References Cited

U.S. PATENT DOCUMENTS

| | | | |
|---|---|---|---|
| 4,688,270 A | 8/1987 | Denicola et al. | |
| 5,048,122 A | 9/1991 | Prieur | |
| 5,293,840 A | 3/1994 | Wedlick | |
| 5,806,096 A | 9/1998 | Pennington | |
| 5,897,519 A | 4/1999 | Shesol et al. | |
| 6,032,289 A | 3/2000 | Villapiano | |
| 6,450,168 B1 | 9/2002 | Nguyen | |
| 6,477,710 B1* | 11/2002 | Ojoyeyi | 2/69 |
| 6,647,552 B1 | 11/2003 | Hogan | |
| 7,073,204 B1 | 7/2006 | Boyles | |
| 7,418,741 B2 | 9/2008 | Rogers | |
| 7,810,172 B2* | 10/2010 | Williams | 2/114 |
| 7,942,856 B2 | 5/2011 | Lentini | |
| 2009/0031471 A1* | 2/2009 | Dague | 2/83 |

* cited by examiner

*Primary Examiner* — Laura Bouchelle
(74) *Attorney, Agent, or Firm* — Grace J. Fishel (57) ABSTRACT

A garment for use with a patient requiring treatment with a central venous catheter and/or gastrostomy tube. Access openings are provided through which the catheter or tube may be reached from the outside of the garment and, in the case of the catheter, coiled on the outside of the garment. Flaps are attached to the garment for covering the access openings and securing the catheter or tube under the flaps. When the access openings are connected with an open ended slot to a central longitudinal opening in the front of the garment, the catheter or tube may be passed into the access opening and the garment put on and taken off without disturbing the medical appliance to which the catheter or tube is attached.

9 Claims, 7 Drawing Sheets

Fig. 1

GARMENT FOR ACCOMMODATING INTRAVENOUS CATHETERS AND GASTRONOMY TUBE

BACKGROUND OF THE INVENTION

1. Field of the Invention

The present invention relates to a garment particularly adapted for use with an infant requiring intravenous or gavage therapy. The garment conceals the catheter or tube on the outside of the garment and allows the garment to be put on and taken off without disturbing the catheter or tube.

2. Brief Description of the Prior Art

Intravenous and gavage therapy are often prescribed in hospitals for premature infants and infants diagnosed with serious illnesses. In the former procedure a central venous catheter is surgically inserted into the patient so that one end is in a large vein leading to the heart and the other end extends out of the body through an aperture in the chest area. The central venous catheter is used to deliver intravenous therapies such as parenteral nutrition, chemotherapy, antibiotics, blood products and other fluids, as well as for blood withdrawal.

In the latter procedure a gastrostomy tube is inserted into an infant's stomach for feeding the infant through the tube, as well as for administering medications. In some instances, an infant may have both a central venous catheter and a gastrostomy tube. For example, a premature infant started with parenteral nutrition introduced through a central venous catheter may as the organs develop begin receipt of enteral nutrition through a gastrostomy tube while continuing parenteral feeding. In other instances the central venous catheter may be needed for other purposes while feeding is through a gastrostomy tube.

In the case of a central venous catheter, the catheter exits the body on the right or left side of the chest and in the case of a gastrostomy tube, the tube exits on the left side in an area below the rib cage. Special needs babies with a central venous catheter and/or gastrostomy tube may be in the hospital for many months and then have therapy for many more months at home under the supervision of a parent or other caregiver. The biggest problem with central venous catheters which go into the heart is infection. Line infections are caused when the line is broken into to change a garment that is soiled. The more times the line is broken into, the greater the risk for infection. A baby on total parenteral nutrition may be given nutrition through a central venous catheter for 18 hours a day and have a bowel movement almost every hour. Babies on total parenteral nutrition also have blow outs and feces can reach the upper neck front and back. This increases the risk of infection if the baby lays in the discharge for several minutes or even an hour or more if the blow out occurs during the night. With currently available garments, the central line must be broken during a diaper change or a clean up after a blow out and, each time, there is a risk of infecting the line.

A central venous catheter may also be accidentally jerked or pulled out. If this occurs and not caught soon enough, a baby can bleed to death. Surgeons suggest taping the central venous catheter to the baby's neck area and back so that the line is out of reach. More commonly the end of the central venous catheter is tucked inside the baby's outfit where it hinders tummy time and irritates the child's skin. With currently available garments, there is no provision for curling up the central venous catheter on the outside of the child's garment such that it does not rub against the baby's skin. Nor is the central venous catheter readily available to perform line maintenance and/or blood draws or administer medications or fluids without waking the baby up. Sick babies are often fussy babies and waking them up may not be ideal for the parents or other caregiver.

There are also problems with gastrostomy tubes. While the risk of infection is less than with a central venous catheter, there is a risk that the tube may be accidentally pulled out of the baby's stomach, causing the baby pain and a trip to the emergency room to install a new tube. With currently available garments, the gastrostomy tube is not protected from being accidentally pulled, nor is the tube accessible without disrobing the baby.

Finally, there is also an issue of appearance and a desire to make the presence of a central venous catheter or gastronomy tube as inconspicuous as possible and to make the baby look as normal as possible. Currently available garments do not meet this requirement either.

BRIEF SUMMARY OF THE INVENTION

In accordance with the invention, a garment for concealing a catheter or tube connected to a medical appliance implanted in a torso of a patient is disclosed. In an embodiment the garment can be put on and removed without disturbing the medical appliance and in all embodiments the garment allows the catheter or tube to be reached from the outside of the garment.

The garment includes a garment body formed from material suitable for clothing having a back portion, arm openings, neck opening and a front portion. The front and back portions are joined at sides thereof and the front portion has first and second front subportions separated by a central longitudinal opening.

There is at least one catheter or tube access opening in one of the first and second front subportions through which the catheter or tube may be passed and a flap laterally attached to the one of the first and second front subportion adjacent to the access opening and movable between open and closed position covering the access opening.

In an embodiment of the garment, an open ended slot is connected to the access opening and extends to the central longitudinal opening through which the catheter or tube may be passed into and out of the access opening. A sheath may be provided along a side of the garment from a point below the access opening and on the same side as the access opening. The sheath is operable to receive the catheter or tube as it emerges from under the flap and secure the catheter or tubing along the side of the garment.

The invention summarized above comprises the constructions hereinafter described, the scope of the invention being indicated by the subjoined claims.

BRIEF DESCRIPTION OF THE SEVERAL VIEWS OF THE DRAWING

In the accompanying drawings, in which several of various possible embodiments of the invention are illustrated, corresponding reference characters refer to corresponding parts throughout the several views of the drawings in which:

FIG. 12 is a plan view of a garment for concealing a central venous catheter exiting on the right side and a gastrostomy tube; and, FIG. 13 is a plan view of a two-piece garment for concealing a central venous catheter existing on the left side and a gastrostomy tube.

DETAILED DESCRIPTION OF THE INVENTION

Referring to the drawings more particularly by reference number, reference numeral 10 refers to a garment in accordance with the present invention. Garment 10 comprises a garment body formed of material suitable for clothing and having a back portion 12, arm openings 14, neck opening 16 and a front portion 18. The front and back portions 18, 12 are joined at sides thereof and the front portion 18 has first and second front subportions 18A, 18B separated at a central longitudinal opening 20.

The particular garment 10 illustrated in the drawings is a body suit commonly called a "onesie." Arm openings 14 include sleeves and the front and back portions 18, 12 are detachably coupled in a crotch portion 22 and include leg openings 24 with pant legs. The "onesie" is an exemplary embodiment of garment 10 but the invention may have application to a variety of hospital and regular garments, including garments for adults as well as children, as they are primarily vehicles for the elements of the invention described below. Suitable garments 10 may have arm and leg openings but no sleeves or no pant legs as well as garments open at the bottom such as a dress or jumper. Garment 10 may be formed of a variety of different materials so long as they provide non-irritating and preferably in the case of infants non-flammable comfort to the wearer.

Central longitudinal opening 20 is closed with releasable fasteners 26, for which plastic snaps are well-suited. Plastic snaps protect patients with nickel allergies from contact with nickel that may be present in metal snaps. The use of plastic snaps also allows garment 10 to be worn during patient x-rays, eliminating the need to disrobe the patient prior to administering an x-ray examination. As used herein, however, releasable fasteners 26 are not limited to plastic snaps and may includes other devices for attaching one thing to another such as for example, a hook-and-loop fastener system, buttons, hooks, catches, latches, buckles, loops, ties, clamps, releasable adhesive and so forth.

Figure 1:
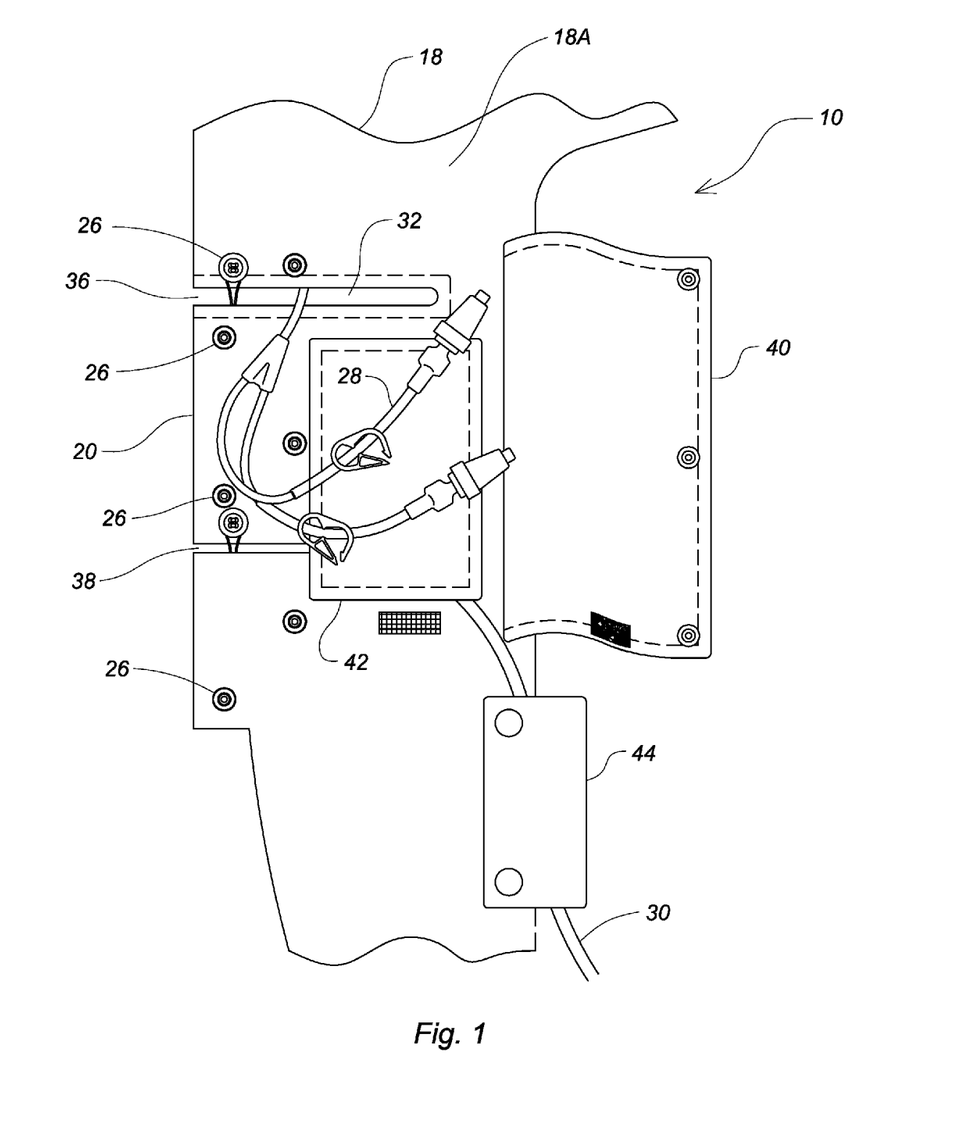
FIG. 1 is a plan detail showing a garment for concealing a central venous catheter exiting on the left side and a gastrostomy tube having open ended slits through which the catheter and tube may be passed to facilitate putting on and taking off the garment without disturbing the medical appliances to which the catheter and tube are attached.
Figures 4, 5:
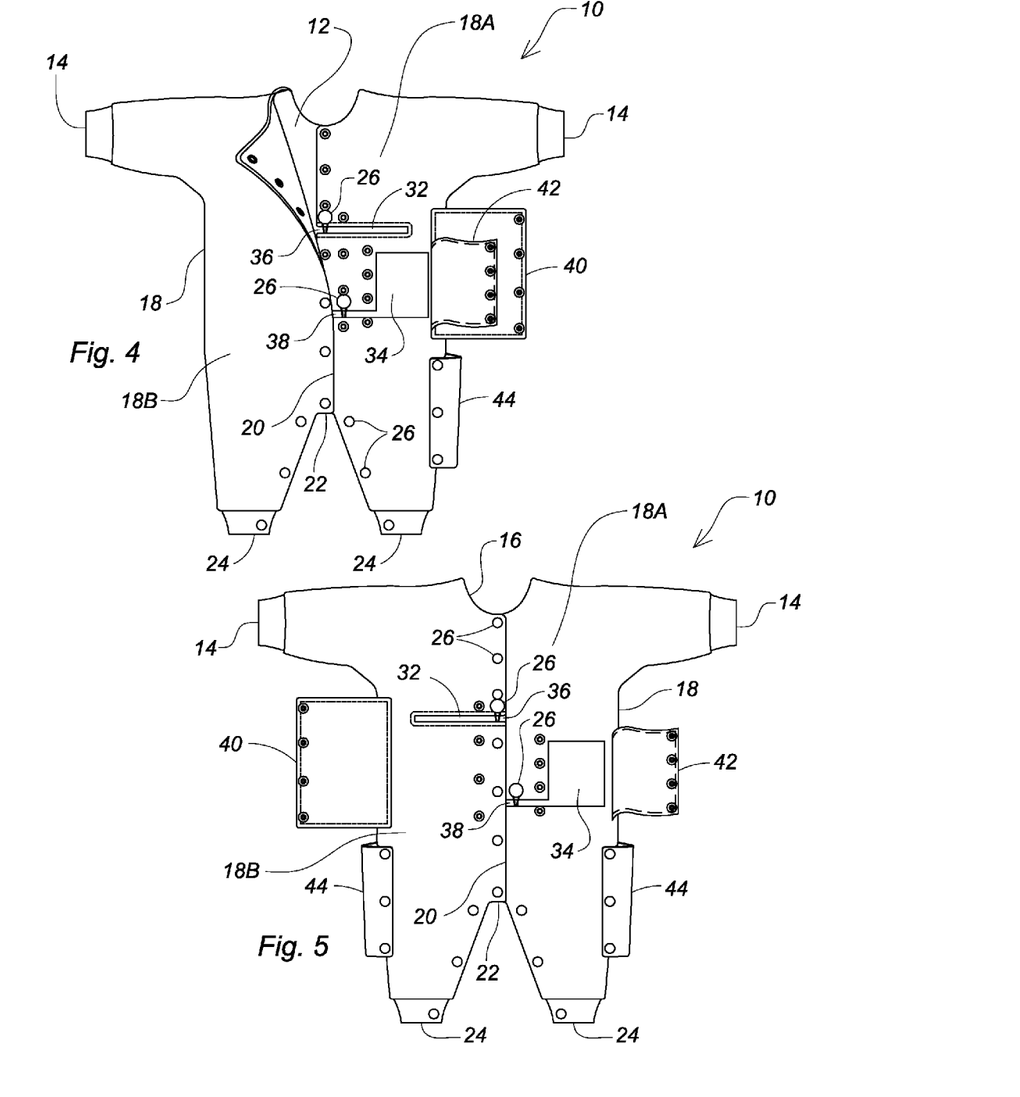
FIG. 4 shows the garment shown in detail in FIG. 1.
FIG. 5 is a plan view of a garment for concealing a central venous catheter exiting on the right side and a gastrostomy tube with open ended slits through which the catheter and tube may be passed.
Figures 6, 7:
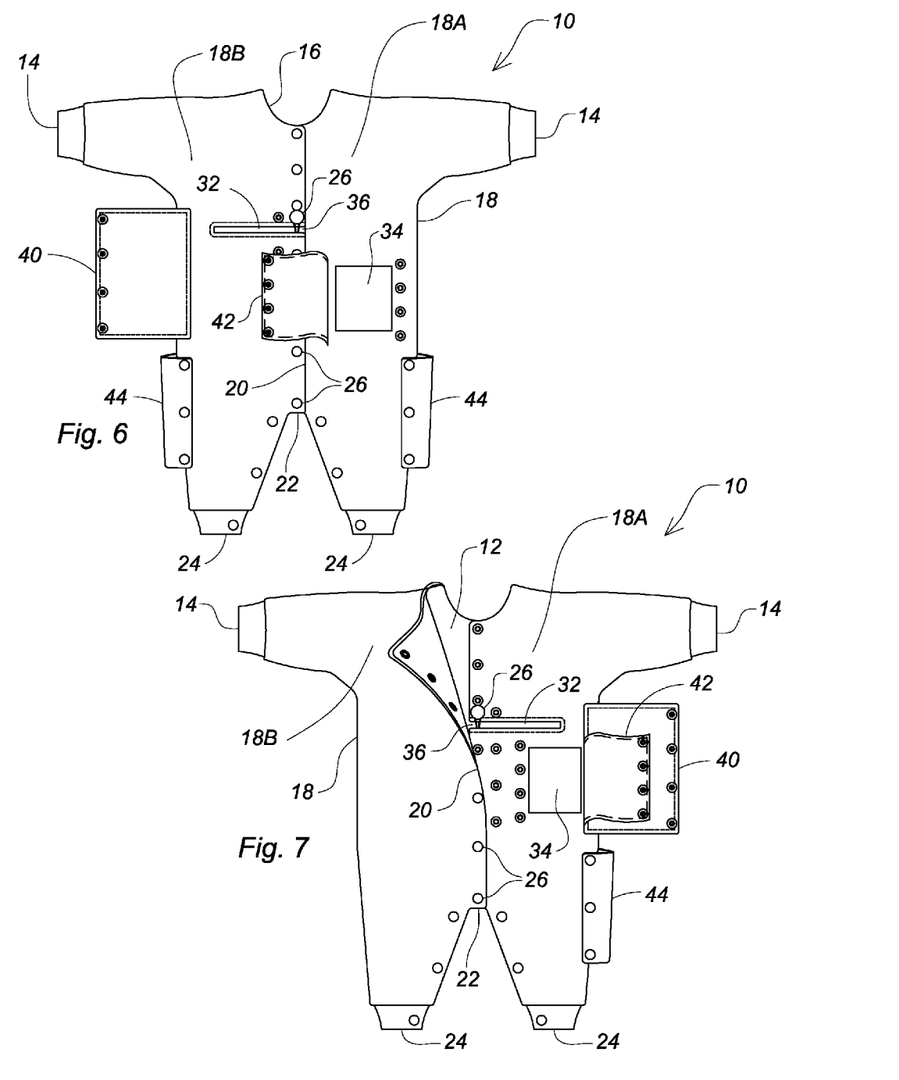
FIG. 6 is a plan view of a garment for concealing a central venous catheter exiting on the right side and a gastrostomy tube with an open ended slot through which the catheter may be passed.
FIG. 7 is a plan view of a garment for concealing a central venous catheter exiting on the left side and a gastrostomy tube with an open ended slot through which the catheter may be passed.

Turning to FIGS. 1 and 4, garment 10 is designed to accommodate an intravenous catheter 28 and a gastrostomy tube 30. The particular intravenous catheter 28 illustrated in FIG. 1 is a double lumen, BROVIAC tunneled central venous catheter. BROVIAC is a registered mark of C. R. Bard, Inc. and its related company BCR, Inc. Other central venous catheters 28 are sold by C. R. Bard, Inc. and by others and have 1, 2 or 3 outside openings. As best seen in FIG. 4, a first access opening 32 is provided in first subportion 18A of front portion 18 through which intravenous catheter 28 may be passed. A second access opening 34 is provided below first access opening 32 through which gastrostomy tube 30 may be passed.

First access opening 32 is formed as an open ended slot 36 extending into central longitudinal opening 20. At central longitudinal opening 20, open ended slot 36 can be closed with a fastener 26 illustrated as a loop-and-button system but including other fasteners as described above. Second access opening 34 is connected to a second open ended slot 38 extending to central longitudinal opening 20. In like manner, second open ended slot 38 may be closed with a loop-and-button system 26.

Figures 8, 8A, 8B, 9:
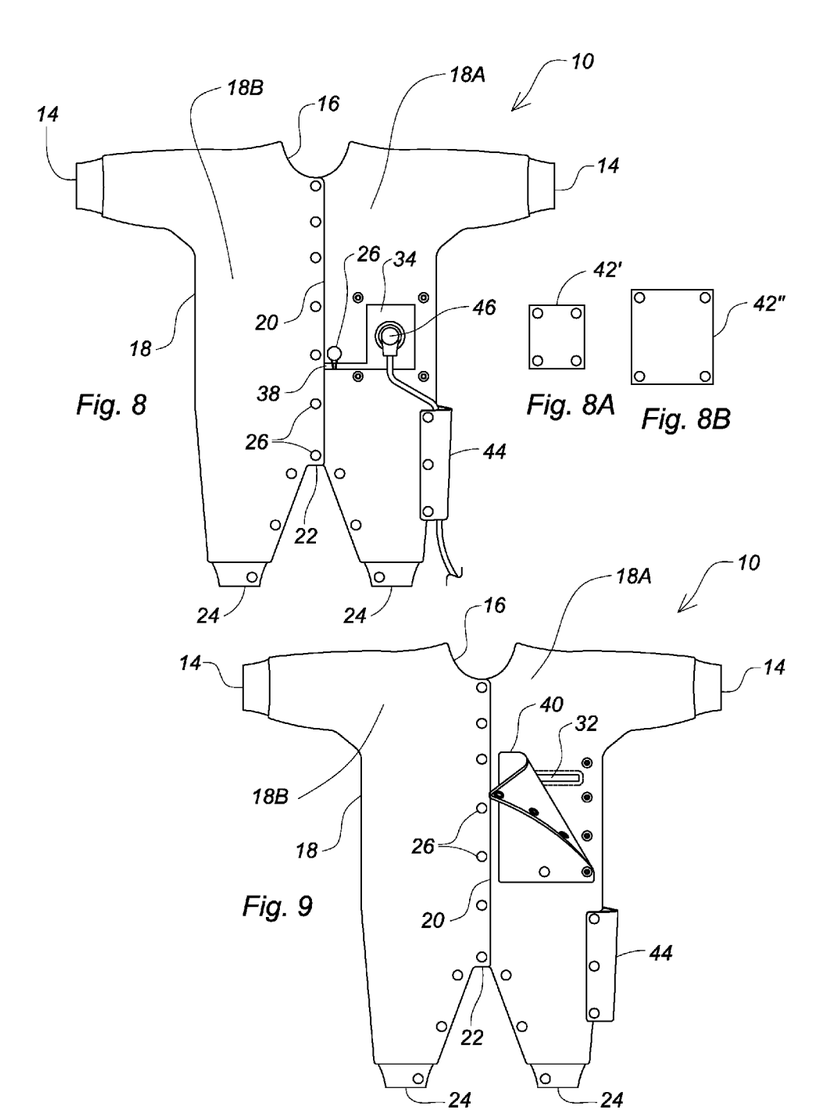
FIG. 8 is a plan view of a garment for concealing a button gastrostomy tube connection with various sized detachable flaps shown in FIGS. 8A and 8B.
FIG. 9 is a plan view of a garment for concealing a central venous catheter exiting on the left side.
Figure 10:
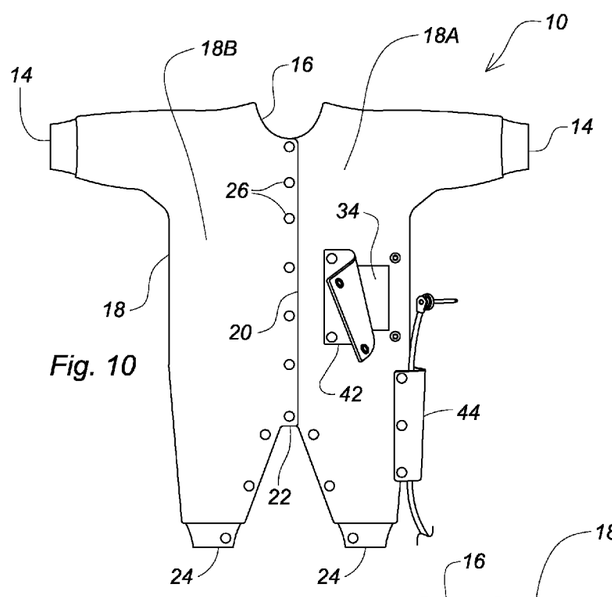
FIG. 10 is a plan view of a garment for concealing a gastrostomy tube.
Figure 11:
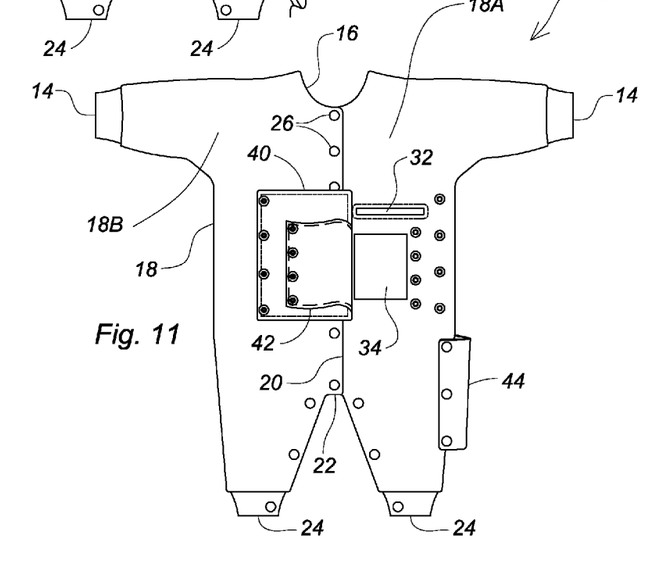
FIG. 11 is a plan view of a garment for concealing a central venous catheter exiting on the left side and a gastrostomy tube.

A first flap 40 is laterally attached to first subportion 18A adjacent first access opening 32 and movable between open and closed position covering the access opening. First flap 40 as shown in FIGS. 1 and 4 may be sewed to first subportion 18A or otherwise permanently attached. As used herein, the term permanently attached means attached in a fashion that requires some level of destruction to detach (e.g., destruction of threads). In other embodiments as shown in FIGS. 8, 8A and 8B, a second flap 42' and 42" may be releasably attached, by which is meant that the flap may be non-destructably detached (e.g., releasing a hook portion from a loop portion of a hook-and-loop fastener system, unsnapping, etc.). In the form illustrated in FIGS. 1 and 4, first flap 40 is large enough to cover second flap 42 which is laterally attached to first subportion 18A adjacent second access opening 34 and movable between open and closed position covering access opening 34.

With continuing reference to FIGS. 1 and 4, a sheath 44 is provided along a side of garment 10 from a point below access openings 32, 34 and on the same side as the access openings. Sheath 44 is operable to receive and secure catheter 28 and tube 30 along the side of garment 10. Sheath 44 includes a fabric panel, one end of which is permanently attached to the side of garment 10 and the other end of which is detachably connected to garment 10 forming a channel into which catheter and tube is received.

The use of garment 10 shown in FIGS. 1 and 4 is as follows with an infant having both a central venous catheter 28 and a gastrostomy tube 30. With both of open ended slits 36, 38 closed with loop-and-button systems 26, central longitudinal opening 20, crotch portion 22 and leg openings 16 are unsnapped. The arms of the infant has passed through sleeves and pant legs and pant legs snapped closed. With first and second flaps 40, 42 open, first one and then the other of open ended slits 36, 38 are opened and the respective catheter 28 or tube 30 passed through the slot and the open ended slot then closed. Central longitudinal opening 20 is then snapped closed before or after crotch portion 22 is snapped closed. With second flap 42 closed BROVIAC catheter 28 is coiled under second flap 42 which is then closed. Sheath 44 is opened, gastrostomy tube 30 inserted and sheath 44 closed. When BROVIAC catheter 28 is uncoiled and connected to a volumetric pump and a bottle or bag, the tube connected to the catheter may also be received in sheath 44.

From the above, it will be apparent that garment 10 is easily put on and by reversing the steps outlined above removed without disturbing the embedded medical appliances to which catheter 28 and tube 30 connect thereby reducing the risk of infection. It will also be apparent that catheter 28 is protected by first flap 40 and tube 30 by sheath 44 from being accidentally disconnected from the medical appliances. Intravenous catheter 28 and gastrostomy tube 30 is concealed and garment 10 has substantially the appearance of an ordinary "onesie."

Figures 2, 3:
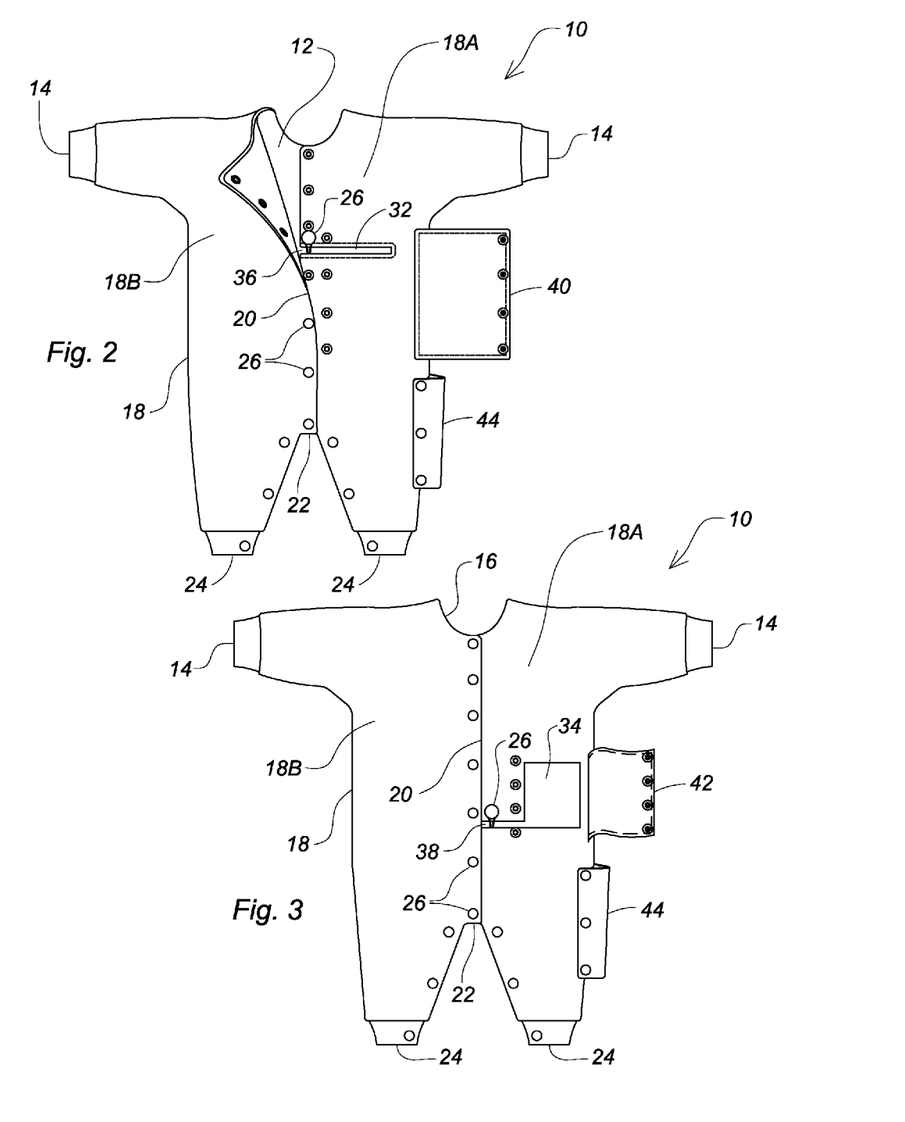
FIG. 2 is a plan view showing a garment for concealing a central venous catheter exiting on the left side with an open ended slot through which the catheter may be passed.
FIG. 3 is a plan view showing a garment for concealing a gastrostomy tube with an open ended slot through which the tube may be passed.

Garment 10 illustrated in FIG. 2 is for an infant having only a central venous catheter 28. It is similar in construction to the garment shown in FIGS. 1 and 4 except that second access opening 34, open ended slot 38 and second flap 42 have been omitted.

Garment 10 illustrated in FIG. 3 is for an infant having only a gastrostomy tube 30. It is also similar in construction to the garment shown in FIGS. 1 and 4 except that first access opening 32, open ended slot 36 and first flap 40 have been omitted.

Garment 10 illustrated in FIG. 5 is for an infant having both central venous catheter 28 and gastrostomy tube 30 wherein the central venous catheter 28 exits the child's chest on the right side instead on the left with the gastrostomy tube 30. A second sheath 44 is provided on the right side of the garment for receipt of tube connected to central venous catheter 28 when in use.

Other of garments 10 shown in FIGS. 6-7 and 9-12 show other possible arrangements where one or both of first and second access openings 32, 34 is not connected to an open ended slot 36, 38. Catheter 28 and tube 30 is accessible outside garment 10 in all of these embodiments.

FIG. 8 illustrates a garment 10 for use with gastrostomy button 46. A feeding tube is connected to the button when feeding occurs and is then removed. The size of the button 46 differs from device to device. To accommodate this different, various sized second flaps 42', 42" as shown in FIGS. 8A and 8B may be provided. For this purpose second flaps 42', 42" may be detachably attached to first subportion 18A as shown.

Figures 12, 13:
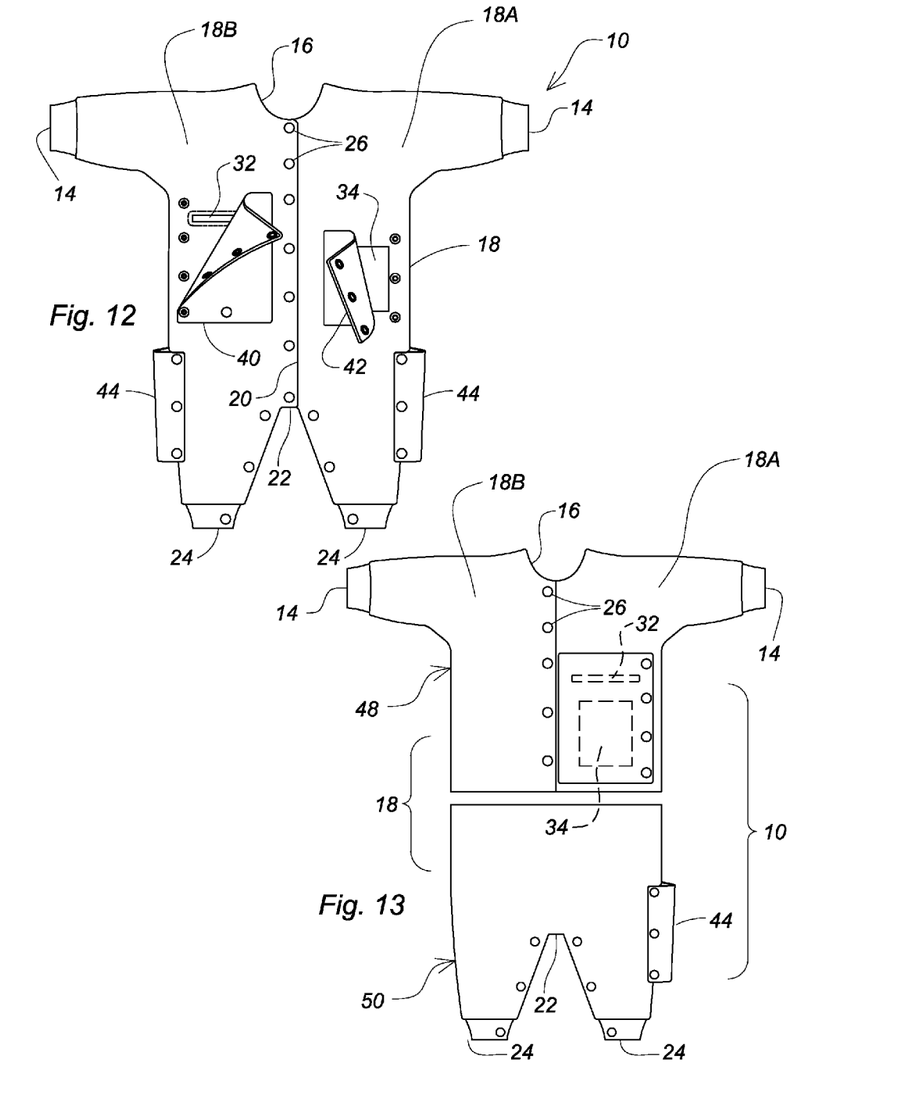

Lastly, FIG. 13 illustrates that garment 10 need not be a one-piece suit but may be formed as a two-piece outfit with a top 48 and a bottom 50.

As various changes could be made in the above constructions without departing from the scope of the invention, it is intended that all matter contained in the above description or shown in the accompanying drawings shall be interpreted as illustrative and not in a limiting sense.

What is claimed:

1. A garment for concealing a central venous catheter connected to a medical appliance implanted in a torso of a patient which allows the garment to be removed without disturbing the medical appliance and allows the catheter to be reached from the outside, said garment comprising a garment body formed from material suitable for clothing having a back portion, arm openings, neck opening and a front portion, said front and back portions joined at sides thereof, said front portion having first and second front subportions separated by a central longitudinal opening which is closable with releasable fasteners, a first access opening in one of the first and second front subportions through which the catheter may be passed and a first flap laterally attached to the one of the first and second front subportions adjacent to the access opening and movable between open and closed position covering the access opening, and said first access opening formed as an open ended slot extending to and terminating at the central longitudinal opening through which the catheter may be narrowly passed, said first flap covering the first access opening and a portion of the front subportion in which the access opening is formed to cover the central venous catheter when disconnected from the medical appliance and curled on the outside of the garment such that it does not rub against the patient's torso.

2. The garment of claim 1 wherein the slot is closed at the central longitudinal opening with a releasable fastener.

3. The garment of claim 2 wherein the releasable fastener is a loop-and-button system.

4. The garment of claim 1 wherein the releasable fasteners for closing the central longitudinal opening are plastic snap fasteners.

5. The garment of claim 1 wherein a second access opening is for a gastrostomy button and a second flap is detachably releasable to the one of the first and second front subportions for covering the second access opening, said second access opening formed as an open ended slot extending to and terminating at the central longitudinal opening through which the tube may be passed.

6. The garment of claim 5 wherein different sized second flaps are provided for different sized gastrostomy buttons.

7. The garment of claim 5 wherein said first flap also covering the second flap.

8. The garment of claim 7 wherein the first and second flaps are held closed with releasable fasteners.

9. The garment of claim 1 further comprising a sheath along a side of the garment from a point below the first access opening and on the same side as the first access opening, said sheath operable to receive the catheter and secure the catheter along the side of the garment.

\* \* \* \* \*